(12) United States Patent
Ataka (10) Patent No.: US 10,088,415 B2
(45) Date of Patent: Oct. 2, 2018

(54) MEASURING PROBE USING TERAHERTZ WAVE

(71) Applicant: ADVANTEST CORPORATION, Tokyo (JP)

(72) Inventor: Tsuyoshi Ataka, Miyagi (JP)

(73) Assignee: ADVANTEST CORPORATION, Tokyo (JP)

( * ) Notice: Subject to any disclaimer, the term of this patent is extended or adjusted under 35 U.S.C. 154(b) by 66 days.

(21) Appl. No.: 15/231,991

(22) Filed: Aug. 9, 2016

(65) Prior Publication Data
US 2017/0074789 A1    Mar. 16, 2017

(30) Foreign Application Priority Data
Sep. 14, 2015    (JP) .................................. 2015-180340

(51) Int. Cl.
G01N 21/35        (2014.01)
G01N 21/3581      (2014.01)

(52) U.S. Cl.
CPC .............................. G01N 21/3581 (2013.01)

(58) Field of Classification Search
CPC .................................................. G01N 21/3581
See application file for complete search history.

(56) References Cited

U.S. PATENT DOCUMENTS

| 5,485,536 | A  | * | 1/1996 | Islam ..................... G02B 6/241 250/311 |
| 6,573,737 | B1 | * | 6/2003 | Lyon ................... G01N 21/3581 324/754.23 |
| 7,315,175 | B2 |   | 1/2008 | Cole |
| 2003/0034453 | A1 |   | 2/2003 | Ookubo et al. |
| 2004/0095147 | A1 | * | 5/2004 | Cole ................... G01N 21/3581 324/629 |
| 2006/0043257 | A1 | * | 3/2006 | Cheng .................... B23K 26/04 250/201.3 |
| 2006/0152232 | A1 | * | 7/2006 | Shvets ............... G01R 31/2822 324/750.02 |
| 2008/0023633 | A1 | * | 1/2008 | Mittleman ................ G01J 3/42 250/341.1 |

(Continued)

FOREIGN PATENT DOCUMENTS

JP    2001-305039    10/2001
JP    2004-522151     7/2004

(Continued)

OTHER PUBLICATIONS

Japanese Office Action for JP App. No. 2015-180340 dated Mar. 16, 2017.

(Continued)

*Primary Examiner* — Casey Bryant
(74) *Attorney, Agent, or Firm* — Greenblum & Bernstein, P.L.C.

(57) ABSTRACT

A probe includes a transmission line support substrate, a probe tip and a probe tip support substrate. The transmission line support substrate supports a transmission line through which a terahertz wave is transmitted. The probe tip transmits the terahertz wave, and is contact with an object to be measured. The probe tip support substrate supports the probe tip. The probe tip support substrate is detachable from the transmission line support substrate.

3 Claims, 9 Drawing Sheets (56) References Cited

U.S. PATENT DOCUMENTS

| | | | |
|---|---|---|---|
| 2008/0309577 A1* | 12/2008 | Mittleman | G01N 21/3581 |
| | | | 343/850 |
| 2010/0218284 A1* | 8/2010 | Jahnke | G01Q 70/06 |
| | | | 850/1 |
| 2010/0235114 A1* | 9/2010 | Levy | G01N 21/9505 |
| | | | 702/40 |
| 2014/0021963 A1 | 1/2014 | Cole | |
| 2015/0028210 A1* | 1/2015 | Han | G01N 21/35 |
| | | | 250/339.06 |
| 2017/0074789 A1* | 3/2017 | Ataka | G01N 21/3581 |

FOREIGN PATENT DOCUMENTS

| | | |
|---|---|---|
| JP | 2006-105972 | 4/2006 |
| JP | 2006-300612 | 11/2006 |
| JP | 2007-240191 | 9/2007 |
| JP | 2008-241711 | 10/2008 |
| JP | 2014-506672 | 3/2014 |
| JP | 2015-028481 | 2/2015 |

OTHER PUBLICATIONS

"Design and Fabrication of a Scanning Near-Field Microscopy Probe with Integrated Zinc Oxide Photoconductive Antennas for Local Terahertz Spectroscopy", Sensors and Materials, May 10, 2010, vol. 22, No. 3, pp. 135-142.

U.S. Appl. No. 15/231,997 to Tsuyoshi Ataka et al., filed Aug. 9, 2016.

\* cited by examiner

MEASURING PROBE USING TERAHERTZ WAVE

BACKGROUND OF THE INVENTION

1. Field of the Invention

The present invention relates to a probe used when an object to be measured is measured by using a terahertz wave.

2. Related Art

There has conventionally been known a measurement of an object to be measured by using the terahertz wave (refer to Japanese Patent Application Laid-Open Nos. 2014-506672, 2007-240191, and 2004-522151). Moreover, the object to be measured is measured by bringing a probe in contact with the object to be measured, thereby supplying the object to be measured with the terahertz wave (refer to Japanese Patent Application Laid-Open Nos. 2014-506672 and 2004-522151).

However, a tip (probe tip) of the probe can preferably be replaced depending on a shape of the object to be measured and the like.

SUMMARY OF THE INVENTION

It is therefore an object of the present invention to provide a probe including a replaceable tip (probe tip).

According to the present invention, a probe includes: a transmission line support substrate that supports a transmission line through which a terahertz wave is transmitted; a probe tip that transmits the terahertz wave, and is contact with an object to be measured; and a probe tip support substrate that supports the probe tip, wherein the probe tip support substrate is detachable from the transmission line support substrate.

According to the thus constructed probe, a transmission line support substrate supports a transmission line through which a terahertz wave is transmitted. A probe tip transmits the terahertz wave, and is contact with an object to be measured. A probe tip support substrate supports the probe tip. The probe tip support substrate is detachable from the transmission line support substrate.

According to the probe of the present invention, the probe tip support substrate may be attached via an intermediate substrate to the transmission line support substrate.

According to the probe of the present invention, a part or an entirety of the probe tip may incline with respect to the probe tip support substrate.

According to the probe of the present invention, the probe tip may be attached to the probe tip support substrate in parallel with the probe tip support substrate.

According to the probe of the present invention, the probe tip support substrate may support the probe tip via a cable.

According to the probe of the present invention, a rise-time filter may be provided for the probe tip support substrate.

DETAILED DESCRIPTION OF THE INVENTION

A description will now be given of embodiments of the present invention referring to drawings.

First Embodiment

Figure 1A:
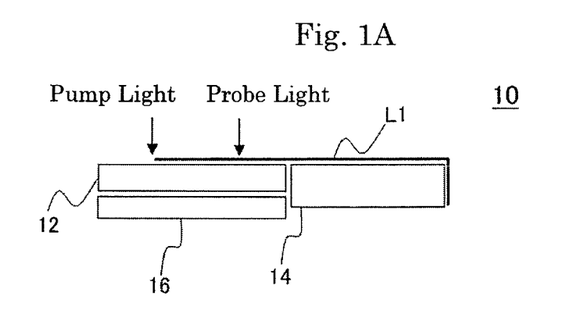
FIGS. 1A, 1B, and 1C are diagrams showing a configuration of a probe 1 according to a first embodiment of the present invention, and respectively show a probe main unit 10 (FIG. 1A), a tip module 20 (FIG. 1B), and a configuration in which the tip module 20 is attached to the probe main unit 10 (FIG. 1C)
Figure 1B:
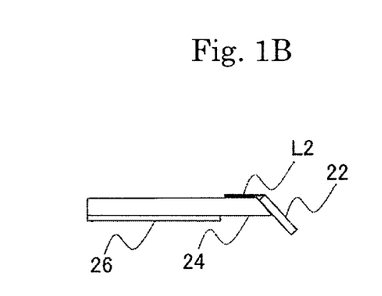
Figure 1C:
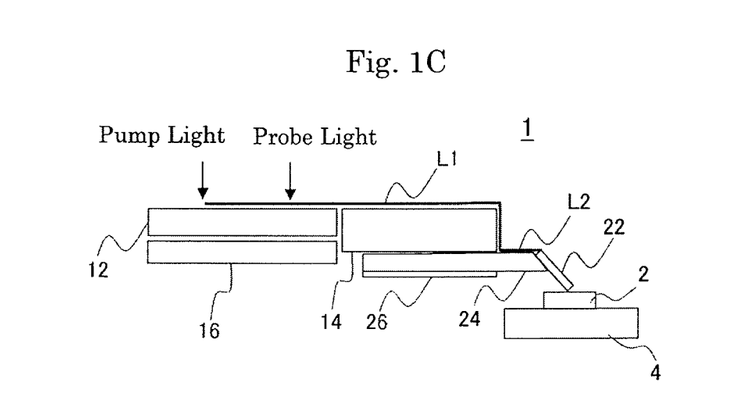

FIGS. 1A, 1B, and 1C are diagrams showing a configuration of a probe 1 according to a first embodiment of the present invention, and respectively show a probe main unit 10 (FIG. 1A), a tip module 20 (FIG. 1B), and a configuration in which the tip module 20 is attached to the probe main unit 10 (FIG. 1C).

The probe 1 according to the first embodiment of the present invention includes the probe main unit 10 and the tip module 20.

Referring to FIG. 1A, the probe main unit 10 includes a transmission line support substrate 12, an intermediate substrate 14, and a main unit GND 16.

The transmission line support substrate 12 supports a transmission line L1. A terahertz wave is transmitted through the transmission line L1. The transmission line L1 is arranged on a top surface of the transmission line support substrate 12.

It should be noted that the transmission line support substrate 12 includes two photoconductive antennas, not shown. One of the photoconductive antennas receives pump light, thereby generating the terahertz wave. This terahertz wave is transmitted through the transmission line L1. This terahertz wave is reflected by an object to be measured 2, and is transmitted through the transmission line L1. The other one of the photoconductive antennas receives probe light, thereby detecting the reflected terahertz wave.

The main unit GND 16 serves to ground the transmission line support substrate 12, and the transmission line support substrate 12 is arranged on the main unit GND 16.

The intermediate substrate 14 is in contact with right ends of the transmission line support substrate 12 and the main unit GND 16. The intermediate substrate 14 supports the transmission line L1. The transmission line L1 is arranged on a top surface and a right end surface of the intermediate substrate 14. It should be noted that a material of the intermediate substrate 14 is $Al_2O_3$ or a resin, for example.

Referring to FIGS. 1B and 1C, the tip module 20 includes a probe tip 22, a probe tip support substrate 24, and a tip module GND 26.

The probe tip support substrate 24 supports a transmission line L2 and the probe tip 22. The transmission line L2 transmits the terahertz wave transmitted through the transmission line L1 to the probe tip 22. Further, the transmission line L2 transmits the terahertz wave, which is made incident from the probe tip 22 to the object to be measured 2, and then is reflected by the object to be measured 2, to the transmission line L1. The transmission line L2 is arranged on a top surface of the probe tip support substrate 24, and connects to the probe tip 22. It should be noted that a material of the probe tip support substrate 24 is $Al_2O_3$ or a resin, for example.

The probe tip 22 transmits the terahertz wave transmitted through the transmission line L1 and the terahertz wave reflected by the object to be measured 2, and is in contact with the object to be measured 2. It should be noted that the entire probe tip 22 inclines with respect to the probe tip support substrate 24. A right end surface of the probe tip support substrate 24 inclines at approximately 45 degrees, and the probe tip 22 is attached on the right end surface.

The probe tip 22 varies in a shape depending on a shape of the object to be measured 2 and the like. The tip module 20 is prepared for each of the shapes of the probe tip 22. It should be noted that the object to be measured 2 is a wire on a substrate 4, for example.

The tip module GND 26 serves to ground the probe tip support substrate 24, and the probe tip support substrate 24 is arranged on the tip module GND 26.

When the object to be measured 2 is measured, the tip module 20 (refer to FIG. 1B) is attached (refer to FIG. 1C) to the probe main unit 10 (refer to FIG. 1A). In more detail, a top surface of the probe tip support substrate 24 is attached detachably (for example, by using bolts and nuts) to a bottom surface of the intermediate substrate 14. Moreover, the transmission line L1 and the transmission line L2 are configured to be in contact with each other. The probe tip support substrate 24 of the tip module 20 is configured to be detachable from the transmission line support substrate 12 of the probe main unit 10 in this way. Moreover, the probe tip support substrate 24 is attached via the intermediate substrate 14 to the transmission line support substrate 12.

A description will now be given of an operation of the first embodiment.

The tip module 20 including the probe tip 22 in the shape suitable for the shape of the object to be measured 2 and the like is attached to the probe main unit 10 (refer to FIG. 1C).

The one photoconductive antenna, not shown, receives the pump light, thereby generating the terahertz wave in the transmission line support substrate 12. The terahertz wave is transmitted through the transmission lines L1 and L2 and the probe tip 22, and is then fed to the object to be measured 2. The terahertz wave fed to the object to be measured 2 is reflected by the object to be measured 2, is transmitted through the probe tip 22 and the transmission lines L2 and L1, and is detected by the other photoconductive antenna, not shown, in the transmission line support substrate 12.

Further, when another object to be measured 2 is measured, the tip module 20 used previously is detached from the probe main unit 10, and a tip module 20 including the probe tip 22 in a shape suitable for the shape of this object to be measured 2 and the like is newly attached to the probe main unit 10 (refer to FIG. 1C).

With the probe 1 according to the first embodiment, the probe tip support substrate 24 of the tip module 20 is detachable from the transmission line support substrate 12 of the probe main unit 10, and the probe 1 enabling the replacement of the tip (probe tip 22) can be provided.

Second Embodiment

The probe 1 according to a second embodiment is different in such a point that the tip module 20 is attached on the intermediate substrate 14 from the first embodiment in which the tip module 20 is attached under the intermediate substrate 14.

Figure 2A:
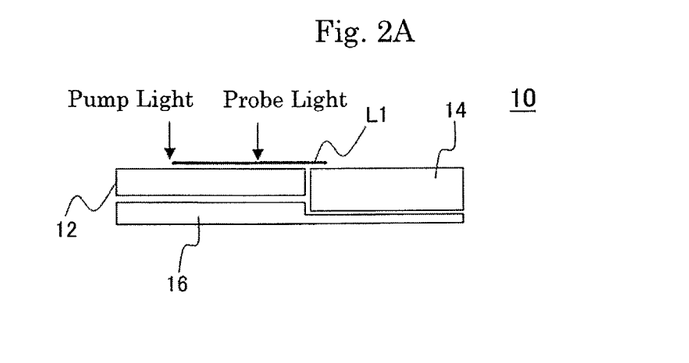
FIGS. 2A, 2B, and 2C are diagrams showing a configuration of the probe 1 according to the second embodiment of the present invention, and respectively show the probe main unit 10 (FIG. 2A), the tip module 20 (FIG. 2B), and the configuration in which the tip module 20 is attached to the probe main unit 10 (FIG. 2C)
Figure 2B:
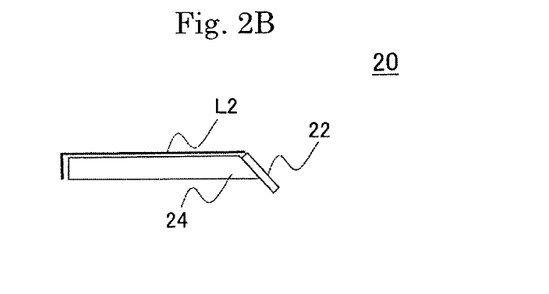
Figure 2C:
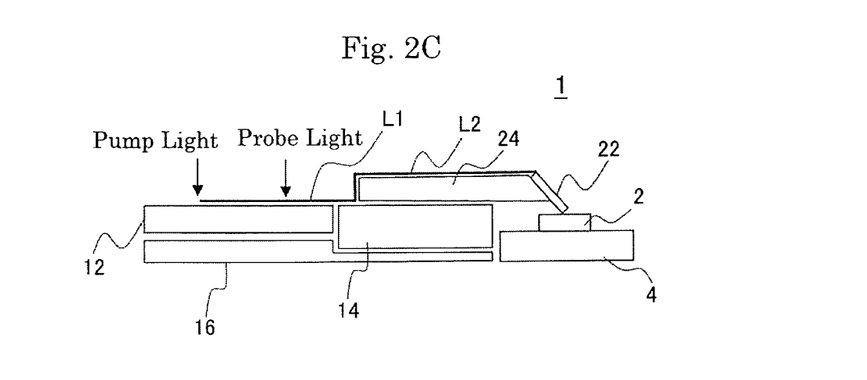

FIGS. 2A, 2B, and 2C are diagrams showing a configuration of the probe 1 according to the second embodiment of the present invention, and respectively show the probe main unit 10 (FIG. 2A), the tip module 20 (FIG. 2B), and the configuration in which the tip module 20 is attached to the probe main unit 10 (FIG. 2C). Hereinafter, like components are denoted by like numerals as of the first embodiment, and will be described in no more details.

The probe 1 according to the second embodiment of the present invention includes the probe main unit 10 and the tip module 20.

Referring to FIG. 2A, the probe main unit 10 includes the transmission line support substrate 12, the intermediate substrate 14, and the main unit GND 16. The transmission line support substrate 12 is the same as that of the first embodiment, and hence a description thereof is omitted.

The main unit GND 16 serves to ground the transmission line support substrate 12 and the intermediate substrate 14, and the transmission line support substrate 12 and the intermediate substrate 14 are arranged on the main unit GND 16.

The intermediate substrate 14 is in contact with a right end of the transmission line support substrate 12. The intermediate substrate 14 supports the transmission line L1. The transmission line L1 is arranged on a top surface of the intermediate substrate 14.

Referring to FIGS. 2B and 2C, the tip module 20 includes the probe tip 22, and the probe tip support substrate 24. The probe tip 22 is the same as that of the first embodiment, and hence a description thereof is omitted. The probe tip support substrate 24 is almost the same as that of the first embodiment, but the transmission line L2 is arranged on the top surface and a left end surface of the probe tip support substrate 24.

When the object to be measured 2 is measured, the tip module 20 (refer to FIG. 2B) is attached (refer to FIG. 2C) to the probe main unit 10 (refer to FIG. 2A). In more detail, a bottom surface of the probe tip support substrate 24 is attached detachably (for example, by using bolts and nuts) to the top surface of the intermediate substrate 14. Moreover, the transmission line L1 and the transmission line L2 are configured to be in contact with each other. The probe tip support substrate 24 of the tip module 20 is configured to be detachable from the transmission line support substrate 12 of the probe main unit 10 in this way. Moreover, the probe tip support substrate 24 is attached via the intermediate substrate 14 to the transmission line support substrate 12.

An operation of the second embodiment is the same as that of the first embodiment, and hence a description thereof is omitted.

According to the second embodiment, there are provided the same effects as in the first embodiment.

It should be noted that though the transmission line L2 arranged on the tip module 20 is arranged along the left end surface and the top surface of the probe tip support substrate 24 according to the second embodiment, it is possible to consider other examples of the arrangement of the transmission line L2.

Figure 3A:
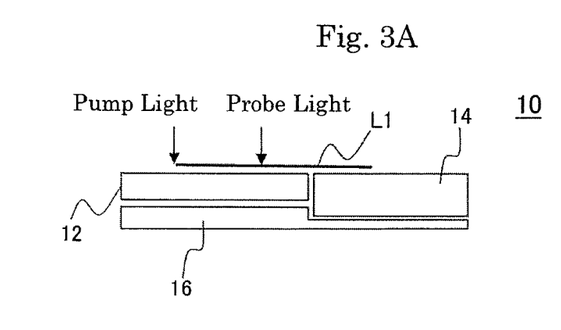
FIGS. 3A, 3B, and 3C are diagrams showing a configuration of the probe 1 according to a first variation of the second embodiment of the present invention, and respectively show the probe main unit 10 (FIG. 3A), the tip module 20 (FIG. 3B), and the configuration in which the tip module 20 is attached to the probe main unit 10 (FIG. 3C)
Figure 3B:
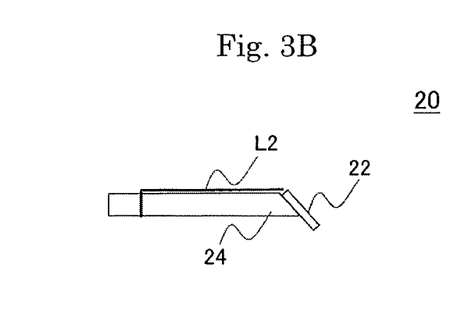
Figure 3C:
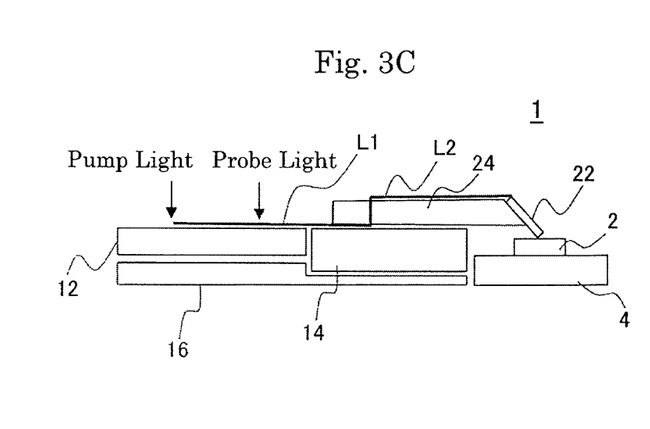

FIGS. 3A, 3B, and 3C are diagrams showing a configuration of the probe 1 according to a first variation of the second embodiment of the present invention, and respectively show the probe main unit 10 (FIG. 3A), the tip module 20 (FIG. 3B), and the configuration in which the tip module 20 is attached to the probe main unit 10 (FIG. 3C).

The transmission line L1 is arranged on the top surfaces of the transmission line support substrate 12 and the intermediate substrate 14. The transmission line L2 vertically passes through the probe tip support substrate 24, and is arranged on the top surface.

Figure 4A:
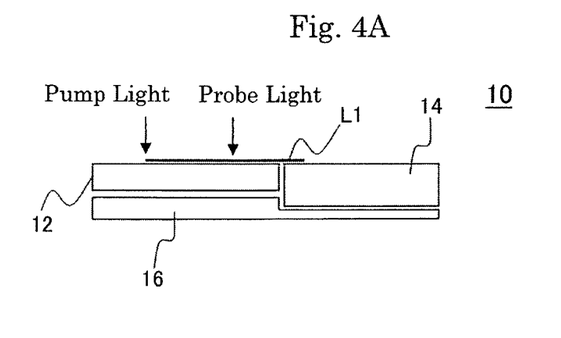
FIGS. 4A, 4B, and 4C are diagrams showing a configuration of the probe 1 according to a second variation of the second embodiment of the present invention, and respectively show the probe main unit 10 (FIG. 4A), the tip module 20 (FIG. 4B), and the configuration in which the tip module 20 is attached to the probe main unit 10 (FIG. 4C)
Figure 4B:
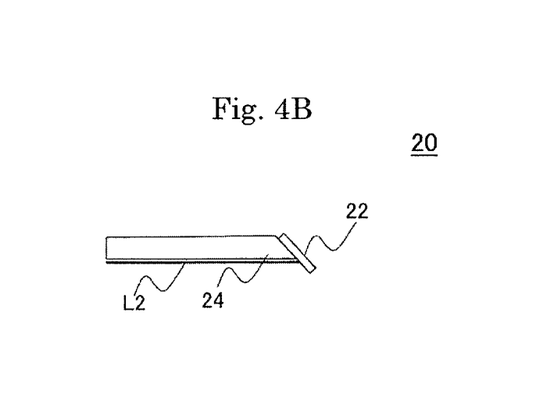
Figure 4C:
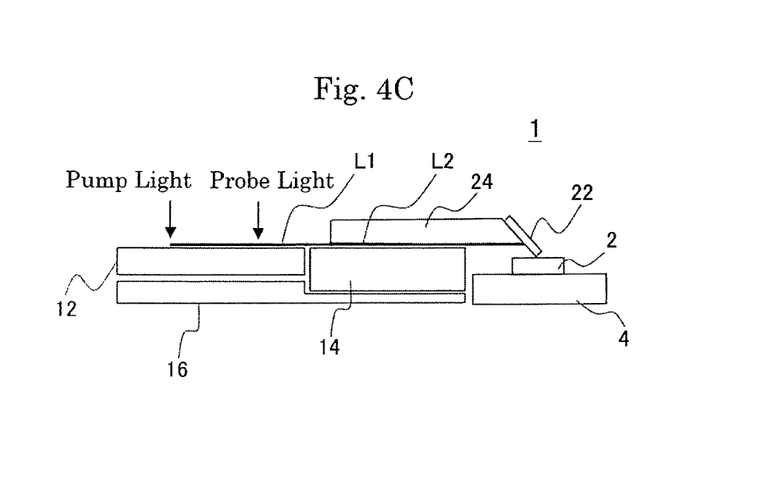

FIGS. 4A, 4B, and 4C are diagrams showing a configuration of the probe 1 according to a second variation of the second embodiment of the present invention, and respectively show the probe main unit 10 (FIG. 4A), the tip module 20 (FIG. 4B), and the configuration in which the tip module 20 is attached to the probe main unit 10 (FIG. 4C).

The transmission line L1 is arranged on the top surfaces of the transmission line support substrate 12 and the intermediate substrate 14. The transmission line L2 is arranged on the bottom surface of the probe tip support substrate 24. Though the transmission line L2 connects to a top end of the probe tip 22 in FIGS. 1, 2, and 3, the transmission line L2 connects to a somewhat lower position of the probe tip 22 in FIG. 4.

Third Embodiment

The probe 1 according to a third embodiment is different in such a point that the tip module 20 is attached to the right end surface of the intermediate substrate 14 from the first embodiment in which the tip module 20 is attached under the intermediate substrate 14.

Figure 5A:
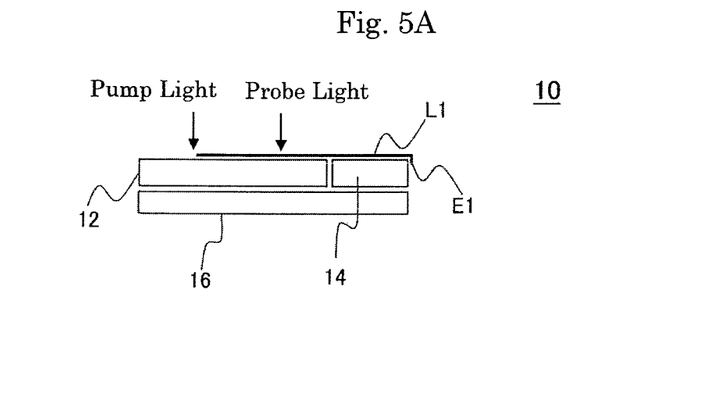
FIGS. 5A, 5B, and 5C are diagrams showing a configuration of the probe 1 according to the third embodiment of the present invention, and respectively show the probe main unit 10 (FIG. 5A), the tip module 20 (FIG. 5B), and the configuration in which the tip module 20 is attached to the probe main unit 10 (FIG. 5C)
Figure 5B:
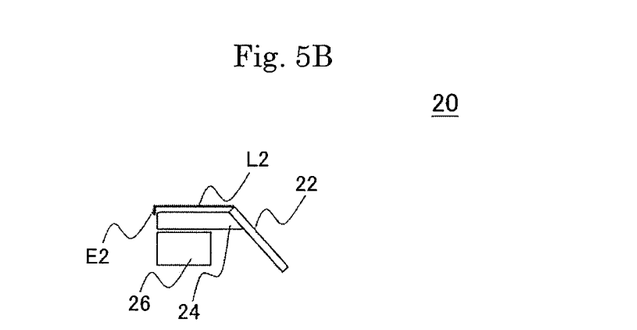
Figure 5C:
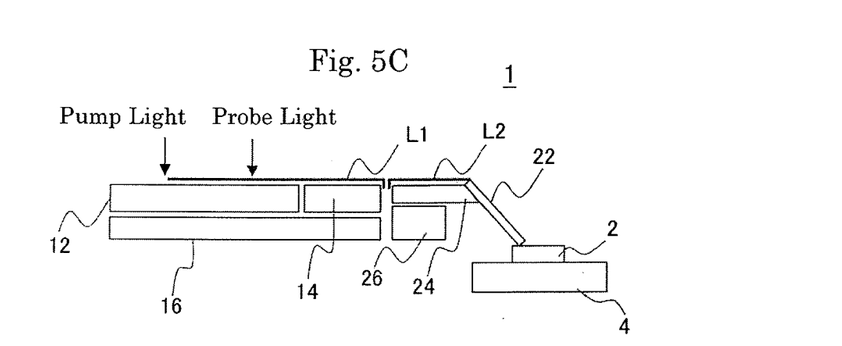

FIGS. 5A, 5B, and 5C are diagrams showing a configuration of the probe 1 according to the third embodiment of the present invention, and respectively show the probe main unit 10 (FIG. 5A), the tip module 20 (FIG. 5B), and the configuration in which the tip module 20 is attached to the probe main unit 10 (FIG. 5C). Hereinafter, like components are denoted by like numerals as of the first embodiment, and will be described in no more details.

The probe 1 according to the third embodiment of the present invention includes the probe main unit 10 and the tip module 20.

Referring to FIG. 5A, the probe main unit 10 includes the transmission line support substrate 12, the intermediate substrate 14, and the main unit GND 16. The transmission line support substrate 12 is the same as that of the first embodiment, and hence a description thereof is omitted.

The main unit GND 16 serves to ground the transmission line support substrate 12 and the intermediate substrate 14, and the transmission line support substrate 12 and the intermediate substrate 14 are arranged on the main unit GND 16.

The intermediate substrate 14 is in contact with the right end of the transmission line support substrate 12. The intermediate substrate 14 supports the transmission line L1. The transmission line L1 is arranged on the top surface of the intermediate substrate 14.

It should be noted that the transmission line L1 includes an electrode E1 on a right end thereof. The electrode E1 is arranged on the right end surface of the intermediate substrate 14.

Referring to FIG. 5B, the tip module 20 is the same as that of the first embodiment, and hence a description thereof is omitted.

It should be noted that the transmission line L2 includes an electrode E2 on a left end thereof. The electrode E2 is arranged on the left end surface of the probe tip support substrate 24.

When the object to be measured 2 is measured, the tip module 20 (refer to FIG. 5B) is attached (refer to FIG. 5C) to the probe main unit 10 (refer to FIG. 5A). In more detail, the left end surface of the probe tip support substrate 24 is attached detachably (for example, by using bolts and nuts) to the right end surface of the intermediate substrate 14. Moreover, the electrode E1 and the electrode E2 are configured to be in contact with each other. The probe tip support substrate 24 of the tip module 20 is configured to be detachable from the transmission line support substrate 12 of the probe main unit 10 in this way. Moreover, the probe tip support substrate 24 is attached via the intermediate substrate 14 to the transmission line support substrate 12.

An operation of the third embodiment is the same as the operation of the first embodiment, and hence a description thereof is omitted.

According to the third embodiment, there are provided the same effects as in the first embodiment.

It should be noted that though the entire probe tip 22 inclines with respect to the probe tip support substrate 24 according to the first, second, and the third embodiments, a part thereof may incline.

Figure 6A:
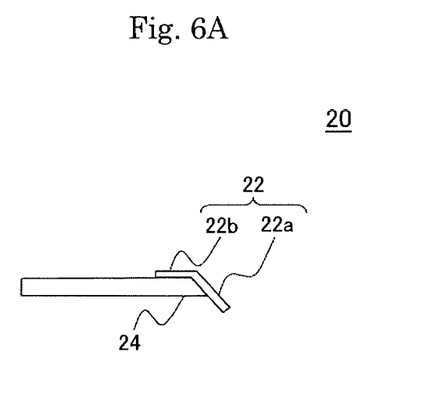
FIGS. 6A and 6B are diagrams showing a first variation in which a part of the probe tip 22 inclines with respect to the probe tip support substrate 24, and respectively show a case in which the right end of the probe tip support substrate 24 inclines (FIG. 6A), and a case in which the right end of the probe tip support substrate 24 does not incline (FIG. 6B)
Figure 6B:
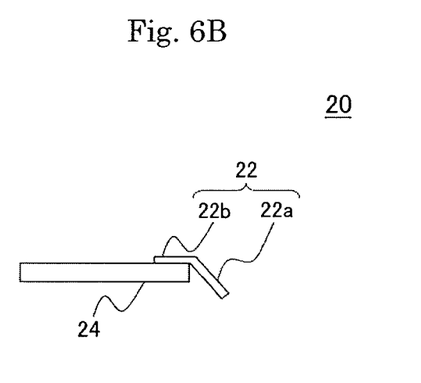

FIGS. 6A and 6B are diagrams showing a first variation in which a part of the probe tip 22 inclines with respect to the probe tip support substrate 24, and respectively show a case in which the right end of the probe tip support substrate 24 inclines (FIG. 6A), and a case in which the right end of the probe tip support substrate 24 does not incline (FIG. 6B). It should be noted that the tip module GND 26 and the transmission line L2 are not shown in FIGS. 6A and 6B.

The probe tip 22 is arranged on the top surface of the probe tip support substrate 24 in the first variation, and can be used as the tip modules 20 in FIGS. 1 to 3 and FIG. 5.

The probe tip 22 according to the first variation includes an inclined portion 22a and a horizontal portion 22b. The horizontal portion 22b is arranged on the top surface of the probe tip support substrate 24. The inclined portion 22a inclines with respect to the probe tip support substrate 24. A right end surface of the probe tip support substrate 24 in FIG. 6A inclines at approximately 45 degrees, and the inclined portion 22a is attached on the right end surface.

Figure 7A:
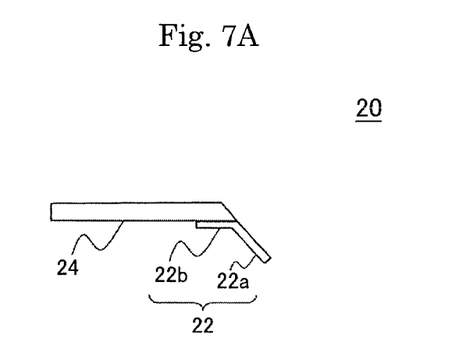
FIGS. 7A and 7B are diagrams showing a second variation in which a part of the probe tip 22 inclines with respect to the probe tip support substrate 24, and respectively show a case in which the right end of the probe tip support substrate 24 inclines (FIG. 7A), and a case in which the right end of the probe tip support substrate 24 does not incline (FIG. 7B)
Figure 7B:
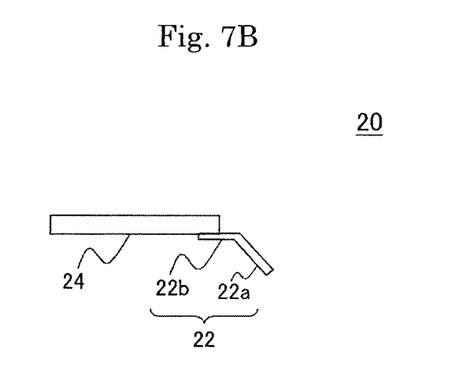

FIGS. 7A and 7B are diagrams showing a second variation in which a part of the probe tip 22 inclines with respect to the probe tip support substrate 24, and respectively show a case in which the right end of the probe tip support substrate 24 inclines (FIG. 7A), and a case in which the right end of the probe tip support substrate 24 does not incline (FIG. 7B). It should be noted that the tip module GND 26 and the transmission line L2 are not shown in FIGS. 7A and 7B.

The probe tip 22 is arranged on the bottom surface of the probe tip support substrate 24 in the second variation, and can be used as the tip module 20 in FIG. 4.

The probe tip 22 according to the second variation includes the inclined portion 22a and the horizontal portion 22b. The horizontal portion 22b is arranged on the bottom surface of the probe tip support substrate 24. The inclined portion 22a inclines with respect to the probe tip support substrate 24. The right end surface of the probe tip support substrate 24 in FIG. 7A inclines at approximately 45 degrees, and the inclined portion 22a is provided along an extension of the right end surface.

It should be noted that though the entire probe tip 22 inclines with respect to the probe tip support substrate 24 according to the first, second, and the third embodiments, the probe tip 22 may be attached to the probe tip support substrate 24 in parallel with the probe tip support substrate 24.

Figure 8A:
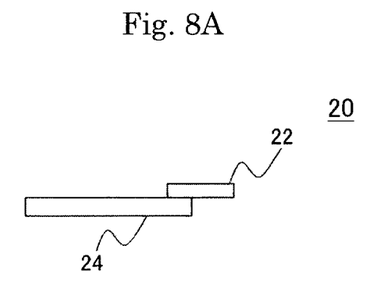
FIGS. 8A and 8B are diagrams showing a third variation in which the probe tip 22 is attached to the probe tip support substrate 24 in parallel with the probe tip support substrate 24, and respectively show a case in which the probe tip 22 is arranged on the top surface of the probe tip support substrate 24 (FIG. 8A) and a case in which the probe tip 22 is arranged on the bottom surface of the probe tip support substrate 24 (FIG. 8B)
Figure 8B:
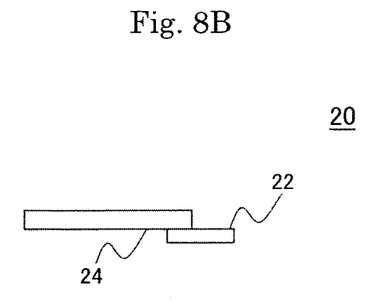

FIGS. 8A and 8B are diagrams showing a third variation in which the probe tip 22 is attached to the probe tip support substrate 24 in parallel with the probe tip support substrate 24, and respectively show a case in which the probe tip 22 is arranged on the top surface of the probe tip support substrate 24 (FIG. 8A) and a case in which the probe tip 22 is arranged on the bottom surface of the probe tip support substrate 24 (FIG. 8B). It should be noted that the tip module GND 26 and the transmission line L2 are not shown in FIGS. 8A and 8B.

The tip module 20 shown in FIG. 8A can be used as the tip modules 20 in FIGS. 1 to 3 and FIG. 5. The tip module 20 shown in FIG. 8B can be used as the tip module 20 in FIG. 4.

Even if the probe tip 22 is attached to the probe tip support substrate 24 in parallel with the probe tip support substrate 24 as in the third variation, the object to be measured 2 can be measured.

Fourth Embodiment

The probe 1 according to a fourth embodiment is different from that according to the third embodiment in such a point that the probe tip support substrate 24 supports the probe tip 22 via a cable 28.

Figure 9A:
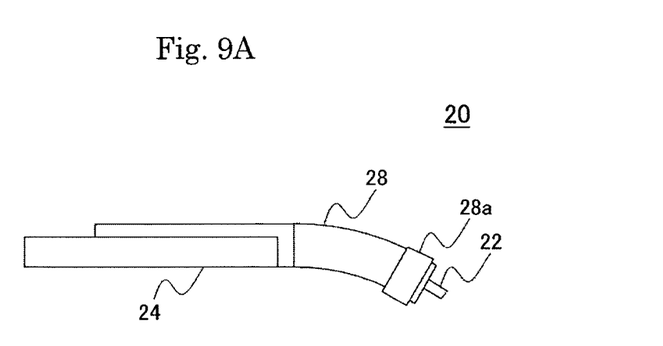
FIGS. 9A and 9B are diagrams showing a configuration of the tip module 20 of the probe 1 according to the fourth embodiment of the present invention, and are respectively a front view (FIG. 9A) and a plan view (FIG. 9B) of the tip module 20.
Figure 9B:
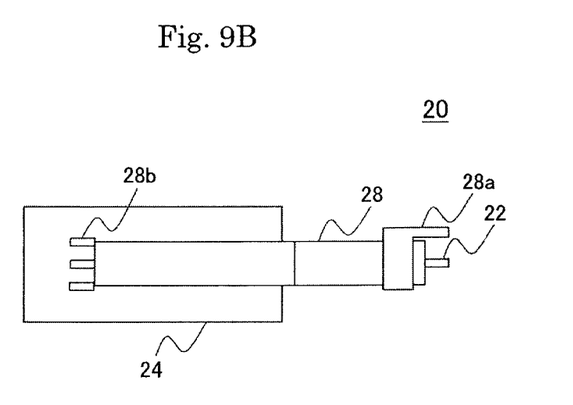

FIGS. 9A and 9B are diagrams showing a configuration of the tip module 20 of the probe 1 according to the fourth embodiment of the present invention, and are respectively a front view (FIG. 9A) and a plan view (FIG. 9B) of the tip module 20. In the following section, like components are denoted by like numerals as of the third embodiment, and will be described in no more details. It should be noted that the tip module GND 26 and the transmission line L2 are not shown in FIGS. 9A and 9B. The probe main unit 10 is the same as that of the third embodiment, and hence a description is omitted.

The tip module 20 according to the fourth embodiment includes the probe tip 22, the probe tip support substrate 24, the tip module GND 26, the cable 28, a grounding contact member 28a, an electrode 28b, and the transmission line L2.

The cable 28 is a semi-rigid cable, and is attached to the top surface of the probe tip support substrate 24. A portion of the cable 28 close to a tip thereof is machined to bend, and thus falls obliquely downward. The probe tip 22 is attached to a center conductor at the tip of the cable 28. The probe tip support substrate 24 uses this structure to support the probe tip 22 via the cable 28.

It should be noted that the ground contact member (GND contact attachment) 28a is attached to the portion close to the tip of the cable 28. Moreover, the tip of the ground contact member 28a is in contact with a ground surface of the substrate 4.

Moreover, the electrode 28b is provided at a rear portion of the cable 28, and is connected to transmission line L2, not shown.

An operation of the fourth embodiment is the same as the operation of the third embodiment, and hence a description thereof is omitted.

According to the fourth embodiment, there are provided the same effects as in the third embodiment.

It should be noted that a waveform a rise of which is suppressed can be fed to the object to be measured 2 by providing a rise-time filter on the probe tip support substrate 24, and connecting the rise-time filter to the transmission line L1 or the transmission line L2 in any one of the embodiments.

What is claimed is:
1. A probe comprising:
A transmission line support substrate that supports a transmission line through which a terahertz wave is transmitted;
a probe tip that transmits the terahertz wave, and is configured to be in contact with an object to be measured; and
a probe tip support substrate that supports the probe tip via a cable,
wherein the probe tip support substrate is removably attached to the transmission line support substrate.
2. The probe according to claim 1, wherein a part of an entirety of the probe tip inclines with respect to the probe tip support substrate.
3. The probe according to claim 1, wherein the probe tip is attached to the probe tip support substrate in parallel with the probe tip support substrate.

* * * * *